(12) United States Patent
Klopotek (10) Patent No.: US 6,325,769 B1
(45) Date of Patent: *Dec. 4, 2001

(54) METHOD AND APPARATUS FOR THERAPEUTIC TREATMENT OF SKIN

(75) Inventor: Peter J. Klopotek, Framingham, MA (US)

(73) Assignee: Collapeutics, LLC, Wellesley, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/340,997

(22) Filed: Jun. 28, 1999

Related U.S. Application Data (63) Continuation-in-part of application No. 08/998,963, filed on Dec. 29, 1998, now Pat. No. 6,113,559.

(51) Int. Cl.⁷ ..................................................... A61N 7/00
(52) U.S. Cl. ................................................................ 601/2
(58) Field of Search ........................ 601/2, 3, 4; 600/439; 604/20, 22; 606/27, 28, 31, 32

(56) References Cited

U.S. PATENT DOCUMENTS

| | | | |
|---|---|---|---|
| 4,372,296 | 2/1983 | Fahim | 128/24 |
| 4,787,373 | 11/1988 | Vogel | 128/24.1 |
| 4,893,624 | 1/1990 | Lele | 128/399 |
| 4,938,216 | 7/1990 | Lele | 128/399 |
| 4,938,217 | 7/1990 | Lele | 128/399 |
| 4,960,109 | 10/1990 | Lele | 128/736 |
| 5,012,797 | * 5/1991 | Liang et al. | 128/24 |
| 5,230,334 | 7/1993 | Klopotek | 128/399 |
| 5,413,550 | 5/1995 | Castel | 601/2 |
| 5,458,596 | 10/1995 | Lax et al. | 606/31 |
| 5,501,655 | 3/1996 | Rolt et al. | 601/3 |
| 5,507,790 | 4/1996 | Weiss | 607/100 |
| 5,569,242 | 10/1996 | Lax et al. | 606/42 |
| 5,618,275 | 4/1997 | Bock | 604/290 |
| 5,755,753 | 5/1998 | Knowlton | 607/98 |
| 5,810,801 | 9/1998 | Anderson et al. | 606/9 |
| 5,964,749 | 10/1999 | Eckhouse et al. | 606/9 |
| 5,983,900 | 11/1999 | Clement et al. | 128/898 |
| 6,113,559 | * 9/2000 | Klopotek | 601/3 |

FOREIGN PATENT DOCUMENTS

| | | |
|---|---|---|
| 2672486 | 8/1992 | (FR). |
| 9108288 | 4/1997 | (JP). |

OTHER PUBLICATIONS

Anvari, B. et al., "Cryogen Spray Cooling in Conjunction With Laser Treatment of Selected Dermatoses," 15th Annual Meeting of the American Society for Laser Medicine and Surgery, San Diego, CA, (Apr. 1995).

Anvari, B. et al., "Selective Cooling of Biological Tissues During Pulsed Laser Irradiation," 15th Annual Meeting of the American Society for Laser Medicine and Surgery, San Diego, CA, pp. 2–4 (Apr. 1995).

Bacon, D.R. and Shaw, A., "Experimental Validation of Predicted Temperature Rises in Tissue–Mimicking Materials," *Phys. Med. Biol.*, vol. 38, 1647–59 (1993).

(List continued on next page.)

Primary Examiner—Marvin M. Lateef
Assistant Examiner—Eleni Mantus Mercader
(74) Attorney, Agent, or Firm—Thomas J. Engellenner; Tram Anh T. Nguyen; Nutter, McClennen & Fish, LLP (57) ABSTRACT

A method and apparatus of reducing skin wrinkles, including applying an acoustic pulse or train of pulses to a subsurface region of human skin without damaging or adversely affecting the surface or epidermis layer of the skin. The pulses cause changes in the dermis layer of the skin that result in enhanced smoothness of the epidermis layer of the skin. In particular, the acoustic pulses are applied to the dermis layer at an amplitude and for a period of time sufficient to induce production of new connective tissue that reduces or eliminate of skin wrinkles.

41 Claims, 7 Drawing Sheets

OTHER PUBLICATIONS

Barnett, S.B. et al., "Current Status of Research on Biophysical Effects of Ultrasound," *Ultrasound in Med. & Biol.*, vol. 20, No. 3, 205–18 (1994).

Chandraratna, P. et al., "Characterization of Collagen by High–Frequency Ultrasound: Evidence for Different Acoustic Properties Based on Collagen Fiber Morphologic Characteristics," *Am. Heart J.*, vol. 133, 364–8 (1997).

Coleman, A.J. and Saunders, J.E., "A Review of the Physical Properties and Biological Effects of the High Amplitude Acoustic Fields Used in Extracorporeal Lithotripsy," *Ultrasonics*, vol. 31, No. 2, 75–89 (1993).

Crum, L.A. et al., "Acoustic Cavitation Produced by Microsecond Pulses of Ultrasound: A Discussion of Some Selected Results," *J. Acoust. Soc. Am.*, vol. 91, No. 2, 1113–9 (Feb. 1992).

Doukas, A. et al., "Biological Effects of Laser–Induced Shock Waves: Structural and Functional Cell Damage In Vitro," *Ultrasound in Med. & Biol.*, vol. 19, No. 2, 137–46 (1993).

Doukas, A., "Laser–generated Stress Waves in Medicine: From Tissue Injury to Drug Delivery," *OSA Trends in Optics and Photonics Series*, vol. 22, 312–6 (Mar. 8–11, 1998).

Doukas, A.G. and Flotte, T.J., "Physical Characteristics and Biological Effects of Laser–Induced Stress Waves," *Ultrasound in Med. & Biol.*, vol. 22, No. 2, 151–64 (1996).

Doukas, A. et al., "Physical Factors Involved in Stress--Wave–Induced Cell Injury: The Effect of Stress Gradient," *Ultrasound in Med. & Biol.*, vol. 21, No. 7, 961–7 (1995).

Enwemeka, C. et al., "The Biomechanical Effects of Low--Intensity Ultrasound on Healing Tendons," *Ultrasound in Med. & Biol.*, vol. 16, No. 8, 801–7 (1990).

Fan, X. and Hynynen, K., "Control of the Necrosed Tissue Volume During Noninvasive Ultrasound Surgery Using a 16–element Phased Array," *Med. Phys.*, vol. 22, No. 3, 297–306 (Mar. 1995).

Gelfand, J. et al., "Alterations in Body Temperature," In *Harrison's Principles of Internal Medicine*, Kurt J. Isselbacher et al., eds. (McGraw Hill), pp. 81–5, 2473–6 (1994).

Grundlagen, A., "Therapeutischer Ultrascha in der Tumortherapie," *Radiologe*, vol. 36, 64–71 (1996).

Lask, G. et al., "Nonablative Laser Treatment of Facial Rhytides," Conference 2870D, *Part of SPIE Proceedings, Cutaneous Applications of Lasers: Dermatology, Plastic Surgery and Tissue Welding*, vol. 2970, 1–12 (Feb. 9, 1997).

Miller, M. et al., "A Review of In Vitro Bioeffects of Inertial Ultrasonic Cavitation From a Mechanistic Perspective," *Ultrasound in Med. & Biol.*, vol. 22, No. 9, 1131–54 (1996).

Milner, T.E. et al., "Dymanic Cooling for Spatial Confinement of Laser Induced Thermal Damage in Collagen," $15^{th}$ Annual Meeting of the American Society for Laser Medicine and Surgery, San Diego, CA, 2–4 (Apr. 1995).

Nyborg, W., "Scientifically Based Safety Criteria for Ultrasonography," *J. Ultrasound Med.*, vol. 11, 425–32 (1992).

Payne, P., "Measurement of Properties and Function of Skin," *Clin. Phys. Physiol. Meas.*, vol. 12, No. 2, 105–29 (1991).

Ramirez, A. et al., "The Effect of Ultrasound on Collagen Synthesis and Fibroblast Proliferation In Vitro," *Medicine and Science in Sports and Exercise*, 326–32 (1997).

Weaver, J. et al., "Mathematical Model of Skin Exposed to Thermal Radiation," *Aerospace Medicine*, 24–30 (Jan. 1969).

Webster, D.F. et al., "The Role of Cavitation in the In Vitro Stimulation of Protein Synthesis in Human Fibroblasts by Ultrasound," *Ultrasound in Med. & Biol.*, vol. 4, 343–51 (1978).

Webster, D.F. et al., "The Role of Ultrasound–Induced Cavitation in the "In Vitro" Stimulation of Collagen Synthesis in Human Fibroblasts," *Ultrasonics*, 33–7 (Jan. 1980).

\* cited by examiner

METHOD AND APPARATUS FOR THERAPEUTIC TREATMENT OF SKIN

REFERENCE TO RELATED APPLICATION

This application is a continuation-in-part of U.S. patent application Ser. No. 08/998,963 filed Dec. 29, 1998 and incorporated herein by reference now U.S. Pat. No. 6,113,559.

BACKGROUND OF THE INVENTION

The present invention relates generally to skin therapy. More particularly, the present invention relates to the use of such therapy for reducing rhytides of the skin (i.e., skin wrinkles), especially facial rhytides.

Human skin is basically composed of three layers. The outer, or visible layer is the stratum corneum. The stratum corneum is essentially a thin layer of dead skin cells that serves, among other things, as a protective layer. Below the stratum corneum is the epidermis layer. The epidermis layer is a cellular structure that forms the outermost living tissue of the skin. Below the epidermis layer is the dermis layer that contains a variety of tissues such as sweat glands, nerves cells, hair follicles, living skin cells, and connective tissue. The connective tissue gives the dermis layer body, shape, and support. Since the epidermis layer lies on top of the dermis layer, the shape, smoothness, and appearance of the epidermis layer is in part determined by the shape of the dermis layer (and largely the connective tissue). Thus, variations in the shape of the connective tissue tend to appear as variations in the epidermis layer.

There are a number of methods currently being used to reduce or eliminate skin wrinkles, particularly facial skin wrinkles. Some of these methods include the use of lasers, cryo-peeling, chemical-peeling, and dermabrasion. These methods appear to stimulate or irritate the dermis layer so that a biological response results that produces new connective tissue which in turn reduces or eliminates skin wrinkles in the treated area.

However, the cryo-peeling, chemical-peeling, dermabrasion and laser ablation methods generally result in significant damage to the epidermis and dermis layers. In these methods, the epidermis layer may be peeled or burned away. This presents several problems: opportunistic infections may invade the dermis layer and thus complicate or prolong recovery; the procedure may cause a patient significant discomfort and pain; and the skin may appear raw and damaged for a significant period of time (on the order of weeks or months) while the healing process takes place. All of these side effects are considered undesirable.

Therefore, one object of the present invention is to provide an improved method and apparatus for reducing or eliminating skin wrinkles.

Another object of the present invention is to provide a method and apparatus for reducing skin wrinkles that does not substantially damage the epidermis layer of the skin.

SUMMARY OF THE INVENTION

The overall concept of the present invention relates to methods and apparatus for therapeutic treatment of skin using ultrasound. In particular, the present invention relates to wrinkle reduction and skin rejuvenation by controlled application of ultrasound energy into the dermis layer. The ultrasound energy triggers a biological response that causes synthesis of new connective tissue in the dermis through activation of fibroblast cells in the dermis without causing or requiring significant irritation or damage to the epidermis. One purpose of the present invention is to provide a cosmetic improvement in the appearance of the skin meaning that the treated skin surface will have a smoother, rejuvenated appearance. The present invention achieves this without the need to induce significant damage to the epidermis layer of the skin.

These and other objects are achieved by the present invention which, in one embodiment, provides a method of rejuvenating human skin, the method comprising applying a focused ultrasound beam to a region of human skin to stimulate or irritate a dermis layer in the region of the skin so as to cause a change in the dermis layer of the skin that results in a change in a smoothness of the epidermis layer of the skin.

According to another embodiment of the invention, an apparatus for rejuvenating human skin is provided, the apparatus comprising an ultrasound transducer, coupled to an ultrasound driver, for propagating ultrasound waves into a region of human skin in response to signals from the ultrasound driver, and a control device constructed and arranged to focus the signals provided by the ultrasound driver circuit to control the ultrasound waves provided by the ultrasound driver so as to stimulate or irritate a dermis layer in the region of the skin to cause a cosmetic improvement in an appearance of the skin.

According to another embodiment of the invention, a transducer configuration, capable of applying focused ultrasound energy to a dermis region of human skin is provided. The transducer configuration comprises a transducer and an acoustical waveguide disposed adjacent to an ultrasound emitting surface of the transducer, wherein a thickness of the acoustical waveguide determines a depth focus of the ultrasound energy in the skin.

According to another embodiment of the invention, a method of rejuvenating human skin is provided, the method comprising applying a focused ultrasound beam to a region of human skin to generate a shock wave to mechanically disrupt a dermis layer in the region of the skin so as to cause a change in the dermis layer of the skin that results in a change in a smoothness of an epidermis layer of the skin.

In a further aspect of the invention, the acoustic pulses which are used to treat the skin have pressure amplitudes that are sufficiently high to introduce non-linearity, that is to say, the speed of propagation of the pulses through the target region of dermis will be higher than the normal speed of sound propagation through skin. For example, in skin, the normal speed of sound is approximately 1480 m/sec. However, at high enough amplitudes, skin tissue becomes more elastic and the speed of propagation can increase to as high as about 1500 m/sec. The magnitude of this non-linear behavior varies not only with pulse amplitude, but also with the duration of the pulse. Typically, the non-linear behavior will be exhibited, with acoustic pulses having intensity (within the target region) of about 500 to about 1000 watts/cm$^2$ and is preferably applied by pulses having durations ranging from about 10 nanoseconds to about 200 microseconds.

One result of this non-linearity is distortion the waveform of the pulses and they travel through the skin, converting waves typically having Gaussian amplitude (pressure) profile to waves that presents a much sharper leading face, essentially a "shock-wave" at the target region below the surface of the skin. In a normal wave propagation mode, there is essentially no net movement of dermal material. However, when acoustic waves exhibit non-linearity, material does move, creating a negative pressure, or vacuum effect, in the tissue in the wake of the pulse. This negative pressure can induce the tissue damage of the present invention, tearing tissue structures apart, heating the region and, thereby, triggering the synthesis of new connective tissue.

The invention is particularly useful for reducing the appearance of human skin wrinkles. Embodiments of the present invention can provide a smoother, rejuvenated appearance of the skin, without adversely damaging the epidermis layer of the skin.

BRIEF DESCRIPTION OF THE DRAWINGS

In the drawings, which are incorporated herein by reference and in which like elements have been given like reference characters.

DETAILED DESCRIPTION

Figure 1:
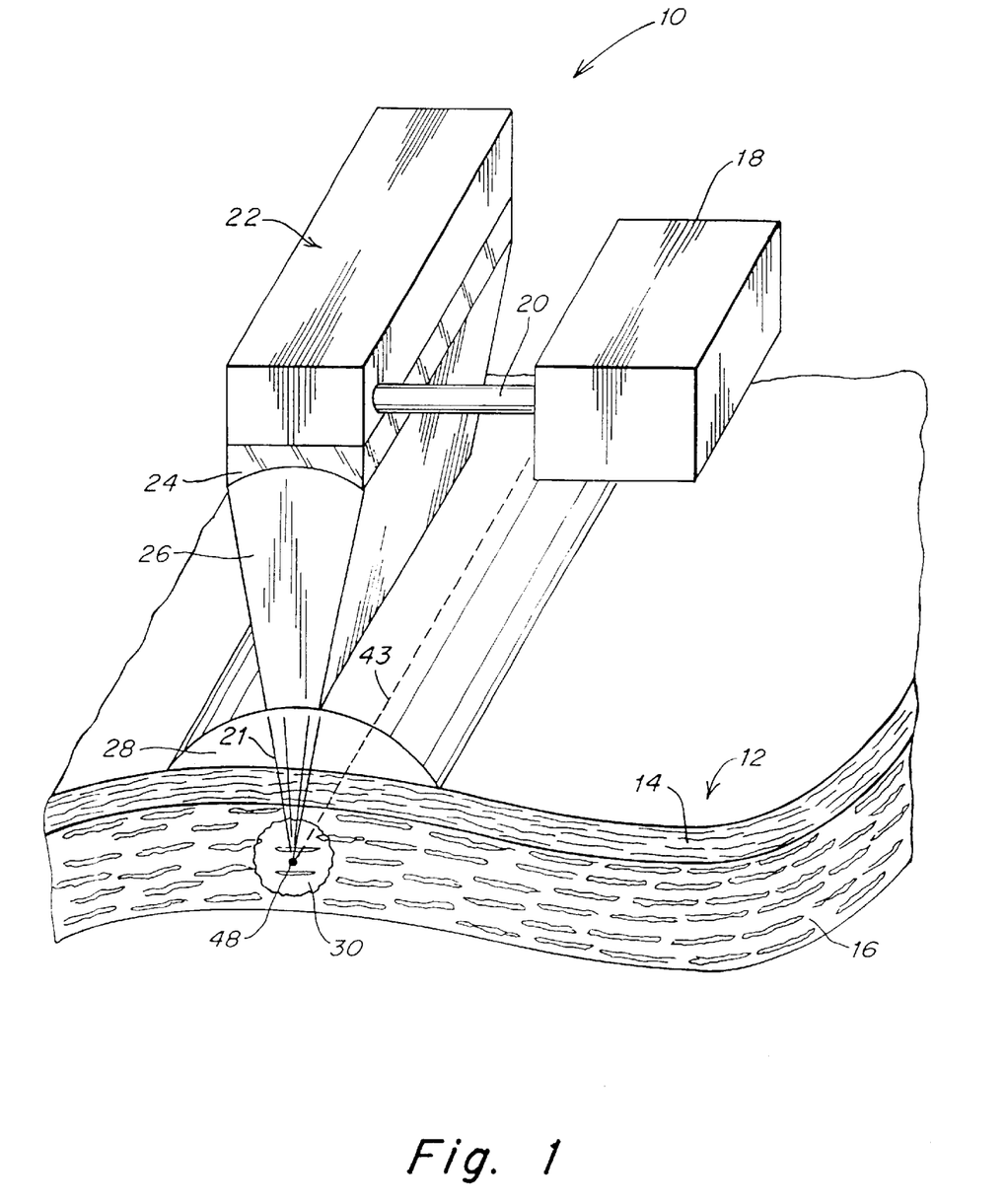
FIG. 1 illustrates one embodiment of an ultrasound generating apparatus according to the invention for reducing skin wrinkles.

FIG. 1 generally illustrates an ultrasound generating apparatus 10 that may be used to apply controlled, localized, focused ultrasound to a region of human skin. The apparatus includes a control circuit 18 coupled to an acoustic wave generator (e.g., an ultrasound transducer) 22 via electrical means 20 which may be a cable or the like. In response to control signals from control circuit 18, transducer 22 generates ultrasound waves 21. Transducer 22 may have one or more elements, such as piezoelectric elements, that actually produce the ultrasound or similar acoustic waves. A focusing element 24, an acoustically-transmitting waveguide 26, and an acoustical coupling medium 28 (either alone or in combination) may also be provided to direct and focus the ultrasound waves produced by transducer 22. Acoustical coupling medium 28 may be a biocompatible hydrogel.

Apparatus 10 is used to direct the ultrasound waves 21 into skin 12. The ultrasound waves are focused using focusing element 24 so that the focused ultrasound waves create a region of stimulation and/or irritation 30 in the dermis layer 16 of skin 12. Focusing ultrasound waves 21 within region 30 allows localized enhancement of the fluence of the ultrasound beam directed into the skin in region 30. This allows a significant part of the energy in ultrasound waves 21 to be substantially absorbed in region 30. This results in stimulation and/or irritation of region 30. Since the region 30 is principally contained in dermis layer 16, there should be little, if any, significant adverse damage to the epidermis layer 14.

The term "ultrasound" as used in this disclosure is intended to encompass both conventional "ultrasound" as typically used to describe high-frequency acoustic waves up to about 100 megahertz and "hypersound" as typically used to describe very high frequency acoustic waves greater than about 100 megahertz. In general, "ultrasound" is used within this disclosure to describe acoustic waves capable of inducing controlled hyperthermia or cavitation in skin tissue, or pulsed waves having an amplitude large enough to induce shock waves in the skin tissue. Hyperthermia, as used in this disclosure, is a condition in which an elevated temperature is induced in a region of the body for therapeutic purposes.

As noted, a feature of the invention lies in providing a focused ultrasound beam that irritates and/or stimulates the dermis layer of the skin without significant or detrimental irritation of the epidermis layer. In FIG. 1, focusing of the ultrasound beam was provided by focusing element 24 which may be a type of lens.

The apparatus illustrated in FIG. 1 is similar to the apparatus described in U.S. Pat. No. 5,230,334, issued to the same inventor. The '334 patent describes a method and apparatus for generating localized hyperthermia in human tissue, particularly in the collagen fibers of the cornea. This previous work has been improved upon by the present invention. One difference lies in the biological mechanism by which the present invention is hypothesized to work. In the '334 patent, the application of relatively high power, controlled hyperthermia, causes the collagen fibers in the cornea to mechanically shrink during the duration of, or immediately after, application of the ultrasound energy to the cornea. This is to be contrasted with the hypothesized mechanism of the present invention in which relatively low power ultrasound is used to gently stimulate and/or irritate the dermis to induce a biological response that results in synthesis or production of new connective tissue over a period of time that extends beyond the time of application of the ultrasound energy. It is envisaged that treatment by the present invention may require multiple treatments extending over a relatively long period of time, such as days, weeks, or months, in order to stimulate the body to produce new connective tissue in the dermis layer and would not cause significant damage to the epidermis. Use of the power levels contemplated in the '334 patent in this manner would cause severe damage to the epidermis.

Figure 2:
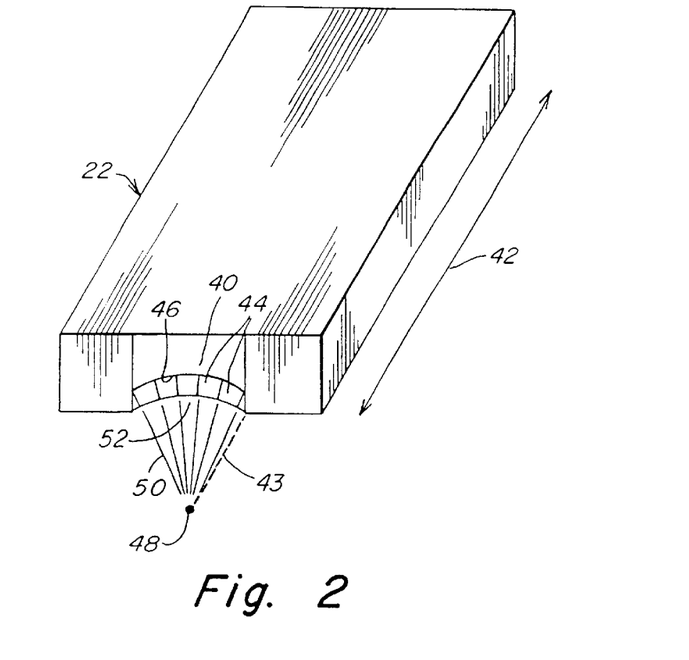
FIG. 2 illustrates one embodiment of an ultrasound transducer that may be used in the invention.

FIG. 2 illustrates another configuration of transducer 22 for providing a focused ultrasound beam. In FIG. 2, transducer 22 has a concave or cylindrical surface 40 that extends along dimension 42. A number of elongated transducer elements, such as piezoelectric elements 44 are disposed along a surface 46 of region 40. One skilled in the art will appreciate that a single curved transducer or multiple transducer elements could be used in transducer 22. Elements 44 extend longitudinally along the direction of dimension 42. Since elements 44 are disposed along the concave surface, they will transmit the ultrasound beams that they respectively generate towards a focal point 48 that lies at the intersection of the various radii 50 that extend from transducer elements 44 to focal point 48. Thus, by adjusting the radius of curvature of surface 46, the location of focal point 48 can be changed. One skilled in the art will appreciate that focal point 48 extends longitudinally along the direction of dimension 42 to create a scanline 43.

Figure 3:
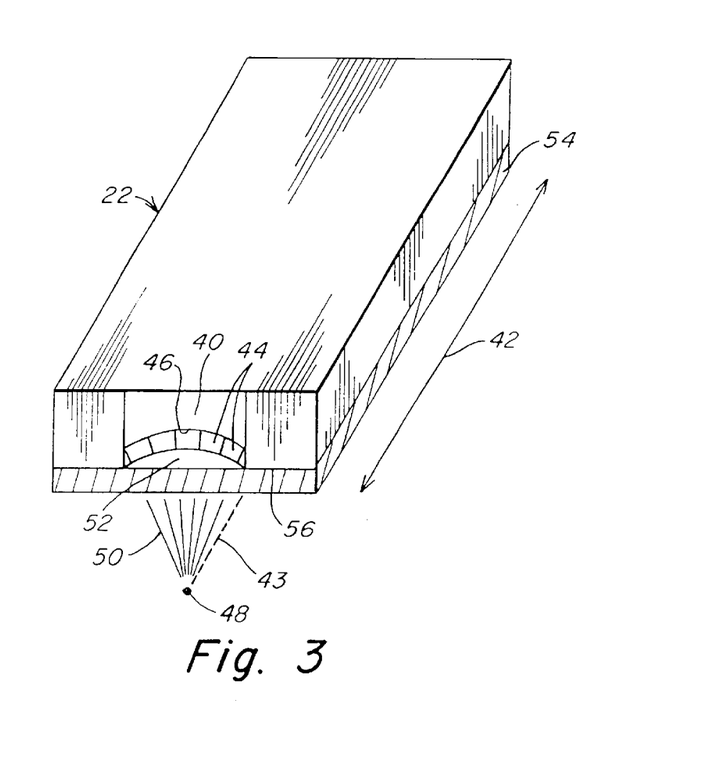
FIG. 3 illustrates another embodiment of a transducer that may be used in the invention.

FIG. 3 illustrates another transducer configuration that can be used in accordance with the present invention. In FIG. 3, transducer 22 is fitted with an acoustical waveguide 54 that covers a surface 56 of the transducer. Acoustical waveguide 54 is analogous to acoustical waveguide 26 illustrated in FIG. 1. An acoustical coupling medium, preferably of a material having the same or similar transmissive properties as acoustical waveguide 54 fills the entire cavity 52. Alternatively, acoustical waveguide 54 can be a single piece that additionally fills cavity 52. The transducer illustrated in FIG. 3 performs in the same manner as transducer 22 illustrated in FIG. 2 however, the addition of acoustical waveguide 54 can make the transducer easier to scan across flat skin surfaces. In addition, acoustical waveguide 54, since it acts to direct the ultrasound waves along the direction of radii 50, can reduce the size and bulk of transducer 22. That is, the addition of acoustical waveguide 54 may allow the radius of curvature of surface 46 to be larger than what would otherwise be required, without waveguide 54, for a given location of focal point 48. Thus, this particular configuration of ultrasound transducer 22 may be easier to manufacture than one having its radius of curvature determined only by the location of focal point 48. This configuration is also useful when higher ultrasound beam intensities are being used because it can prevent overheating of the transducer since the transducer can be made physically larger to better dissipate heat.

In the present invention, the depth of focus of scanline 43 is very close to the surface of the skin, therefore, acoustical waveguide 54 can be used to determine the depth of focus. Acoustical waveguide 54 can be of differing thickness where each different thickness provides a different depth of focus. Use of acoustical waveguides of differing thickness provides a convenient means for changing the depth of focus which can be advantageous in the case where treatment is carried out in, for example, a doctor's office.

Figure 4:
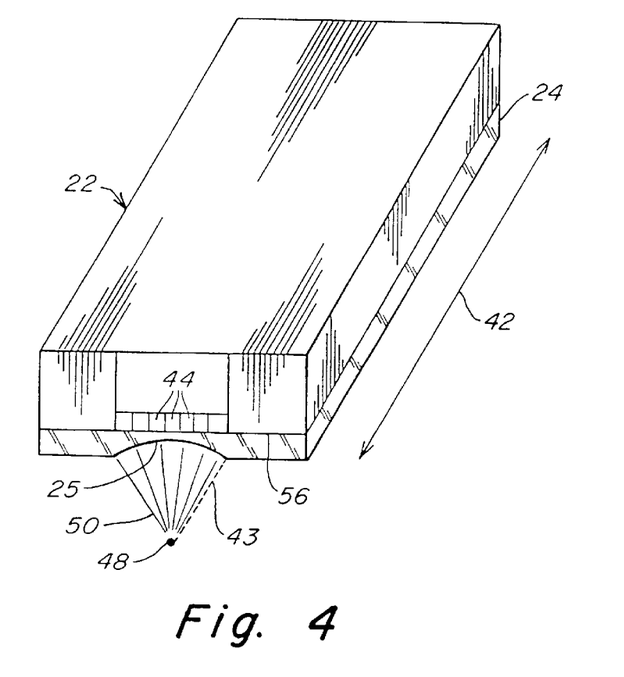
FIG. 4 illustrates another embodiment of a transducer that may be used in the invention.

FIG. 4 illustrates another transducer configuration that can be used in accordance with the present invention. In FIG. 4, transducer 22 has a flat or planar configuration and transducer elements 44 are disposed in an essentially planar fashion. A lens 24 having a focusing portion 25 is disposed along the lower surface 56 of the transducer. Focusing section 25, which is cylindrical and extends along the direction 42, acts to focus the ultrasound wave generated by transducer elements 44 along the direction of lines 50 so that the ultrasound waves produced by transducer elements 44 are focused at focal point 48.

Figure 5:
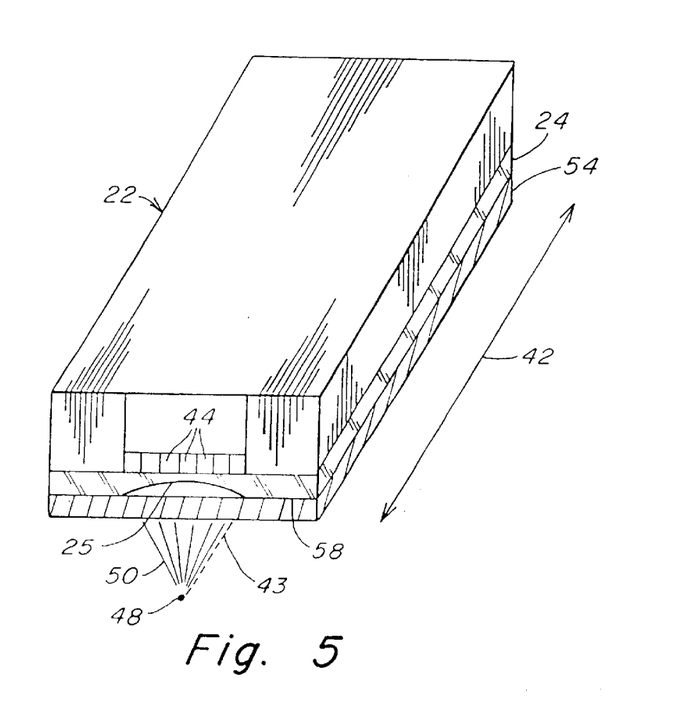
FIG. 5 illustrates another embodiment of a transducer that may be used in the invention.

FIG. 5 illustrates another transducer configuration that can be used in accordance with the present invention. In FIG. 5, transducer 22 is fitted with an acoustical waveguide 54 disposed at the lower surface 58 of lens 24. Acoustical waveguide 54, in the same manner described in connection with FIG. 3, allows the radius of curvature of focusing section 25 of lens 24 to have a larger radius of curvature than would otherwise be required for a given location of focal point 48. Thus, this particular configuration of ultrasound transducer 22 may be easier to manufacture.

The systems illustrated in FIGS. 1, 2, 3, 4, and 5 should strongly focus the ultrasound beam with a numerical aperture in the range of approximately 0.1 to approximately 0.95. As illustrated in the figures, the lens preferably has a cylindrical geometry.

One skilled in the art will also appreciate that a biocompatible hydrogel may be placed between the skin surface and the lens 24 (in the case of FIG. 4) and acoustical wave guide 54 (in the case of FIG. 5).

One skilled in the art will appreciate that although particular transducer configurations have been illustrated in FIGS. 1–5, a variety of other transducer configurations can be used in the present invention. In addition, a phased array ultrasound transducer could be used. A phased array may be advantageous in that it can be used to focus the ultrasound beam generated by each respective transducer element at a desired focal point depth and location. In addition to focusing the ultrasound beam, the phased array can be used to scan the ultrasound beam over the area of skin to be treated.

Figure 6:
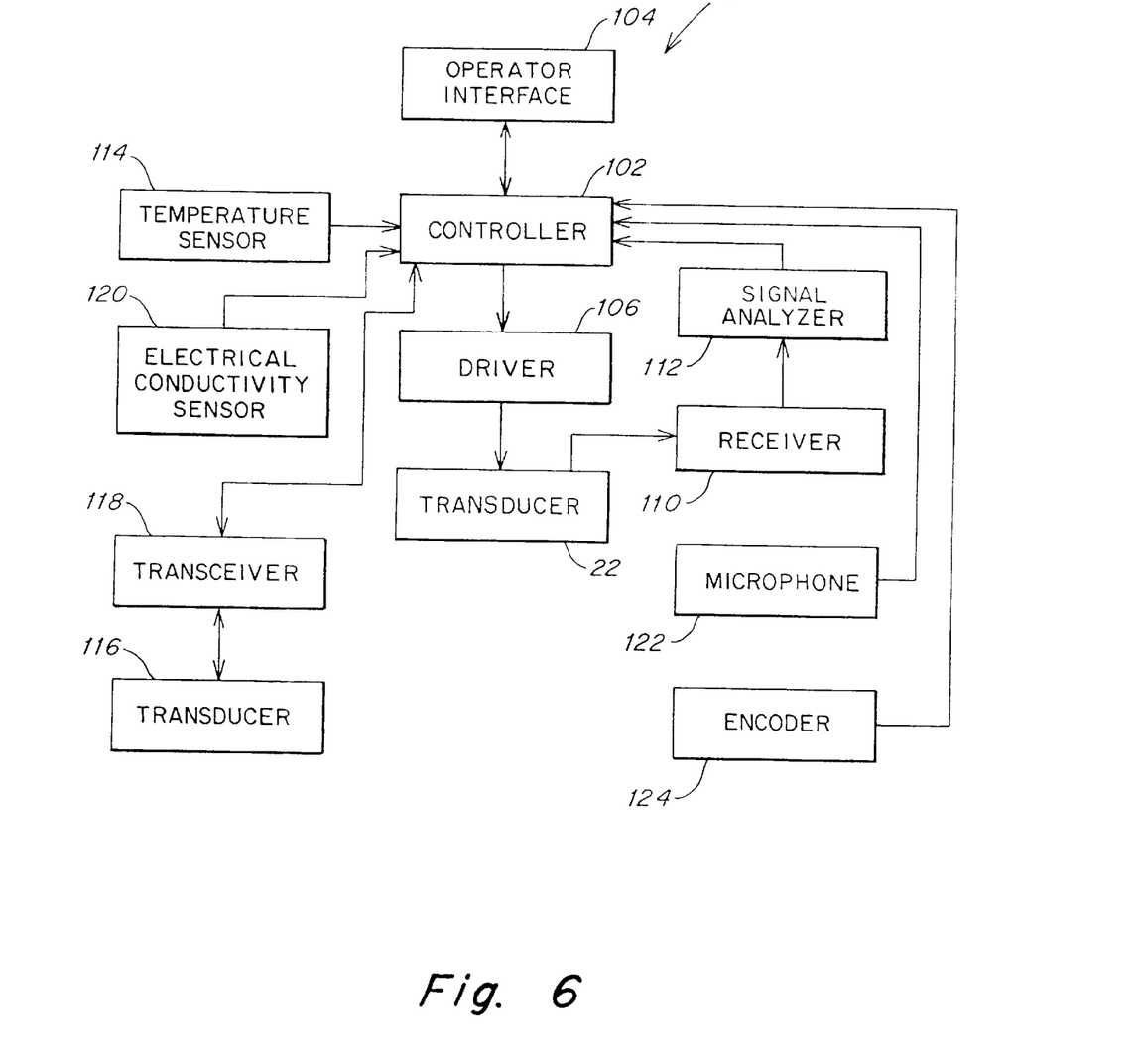
FIG. 6 illustrates a control system that may be used to control the apparatus illustrated in FIG. 1.

FIG. 6 illustrates a control system that may be used in the present invention to control the amount of energy provided to region 30 of dermis layer 16. The control system 100 includes a controller 102. Controller 102 may include a computer and associated peripherals such as memory and mass storage devices. An operator interface 104, which may include at least a keyboard and display device, allows the user to set various parameters such as the focal point depth, the magnitude of the ultrasound beam to be applied, the duration that the ultrasound beam will be applied, and so on. Control signals from controller 102 are sent to a driver 106. Driver 106 contains means, such as circuitry, such as needed to cause the transducer element or elements of transducer 22 to generate ultrasonic waves.

Control system 100 thereafter includes five different feedback systems that may be used to control the dose of ultrasound energy applied to a patient's skin. One skilled in the art will appreciate that the five feedback systems may be used individually or in any combination.

The first feedback system includes a receiver 110 and a signal analyzer 112. Receiver 110 and signal analyzer 112 may be used to measure the magnitude of the ultrasound energy being applied to the patient's skin and to provide a feedback signal to controller 102 to automatically, or allow the operator to manually adjust the magnitude of the ultrasound beam being delivered by transducer 22.

The second feedback system includes a temperature sensor 114 that may be used to measure the temperature of the skin in the region where the ultrasound energy is being applied. Using temperature sensing as a feedback mechanism can be effective because the surface of the skin where temperature sensor 114 would be located is in close proximity to the region of the skin being heated by ultrasound energy. The sensed temperature reading can then be used by controller 102 to automatically, or manually, under control of the operator, to control the magnitude of ultrasound energy being delivered to the patient's skin by transducer 22.

The third feedback system includes a second ultrasound transducer 116 and transceiver 118. Transceiver 118 and transducer 116 can be used to provide a low level ultrasound signal that can be used for diagnostic and feedback purposes to controller 102. Transceiver 118 and transducer 116 can also be used as an echolocating system for target location. That is, the low power ultrasound signals can be used to locate microorgans, such as hair follicles, in the skin to aid in treatment.

Furthermore, if driver 106 is replaced with a transceiver or if an additional receiver is provided and connected to transducer 22 and controller 102 then the echolocating function can be performed using one transducer. That is the transducer 22 may be placed on the patient's skin and, under control of controller 102, low power ultrasound waves can be used for target location and placement. Once a location for treatment has been established, controller 102 can be switched to a treatment mode and a higher power ultrasound wave may then be applied using transducer 22 to treat the skin.

More generally, the low power ultrasound may be used to locate a condition below the epidermis that causes an irregularity in the smoothness of the epidermis. Higher power ultrasound can then be used to treat the area.

Furthermore, the low power ultrasound signal can also be used to automatically determine the depth of focus for the ultrasound energy. For example, the low power or diagnostic ultrasound signal can be used to locate the depth of the interface between the dermis and the epidermis in the area to be treated. The depth of focus for the high power or therapeutic ultrasound can then be set based on this measurement to ensure that the ultrasound energy is focused in the dermis layer.

The fourth feedback system includes an electrical conductivity sensor 120 that may be used to measure the electrical conductivity of the patient's skin in the region where the ultrasound energy is being applied. The degree of electrical conductivity sensed by sensor 120 can then be used by controller 102 to automatically, or manually, under control of the operator, control the magnitude of ultrasound energy being delivered to the patient's skin by transducer 108.

The fifth feedback system includes a broadband microphone 122 connected to controller 102. When cavitation is used as a mechanism to provide dermal irritation, microphone 122 can be placed on or near the skin in the region being treated. The collapse of a bubble created by application of ultrasound in the dermis creates a characteristic audible sound that is detected by microphone 122. The signal provided by microphone 122 can then be used by controller 102 with appropriate signal processing to control the ultrasound energy provided by transducer 22. The user can also listen to the signal provided by microphone 122 and manually control the ultrasound energy.

Controller 102 should be programmed so that transducer 22 delivers a spatially uniform ultrasound dosage in the area of the skin that is being treated to ensure uniform stimulation of the dermis layer. The method of the invention appears to be most effective when there is, on average, a homogeneous deposition of energy in the region of the skin that is being treated.

Figure 7:
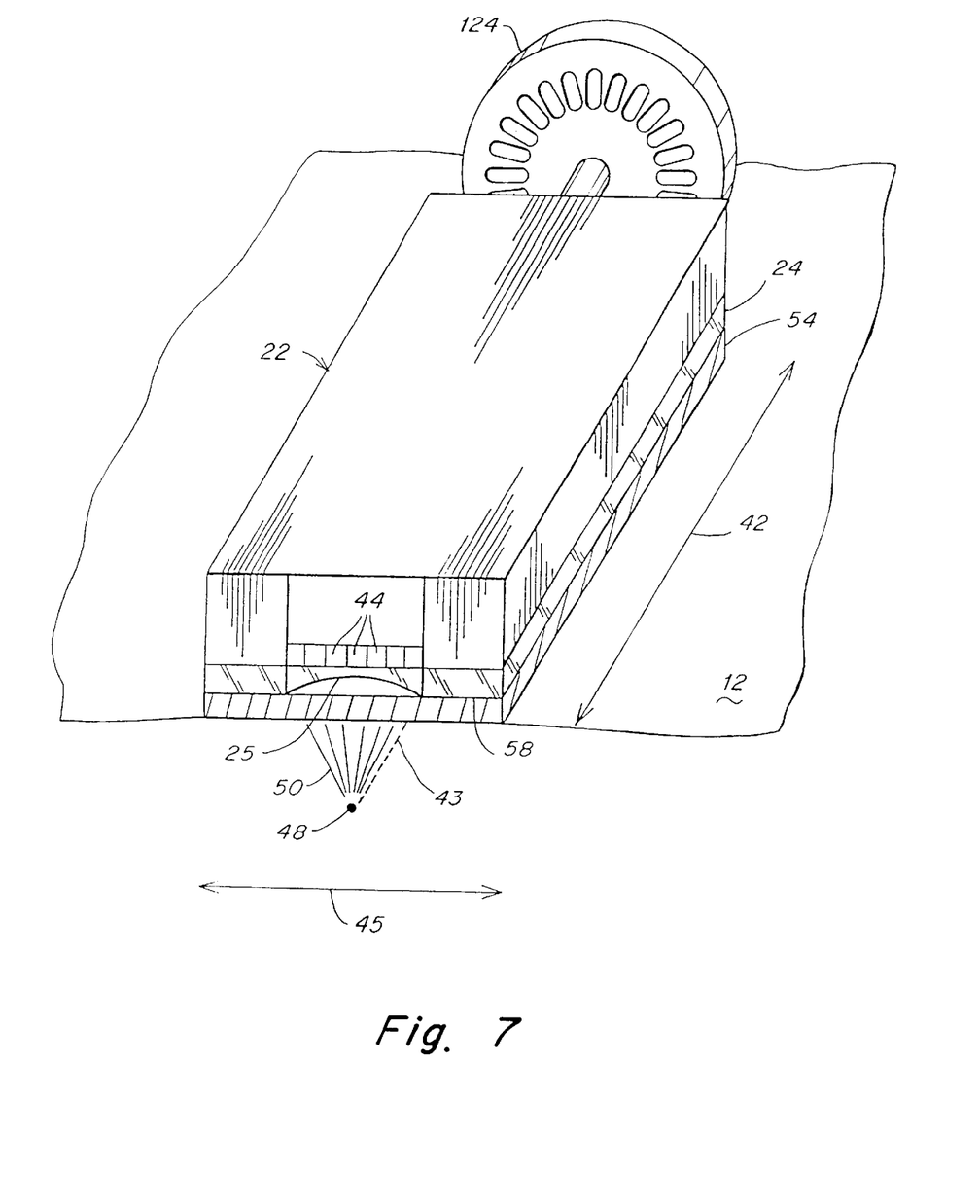
FIG. 7 illustrates another embodiment of a transducer that may be used in the invention.

Referring to FIG. 7 transducer 22 is illustrated as being scanned along a direction defined by double-headed arrow 45. While transducer 22 is being scanned along the direction of arrow 45, it is delivering an ultrasound beam focused at a focal point or depth 48 in the dermis layer of the skin. Focal point 48 extends longitudinally along the direction of dimension 42 to create a scanline 43. Controller 102 therefore needs to be programmed to deliver a uniform level of energy in two dimensions; one along the direction or dimension 42 and one in a direction of scanning along line or dimension 45.

The energy delivered by transducer 22 into the skin may be delivered in a continuous manner or in discrete increments. One skilled in the art will appreciate that the ultrasound energy may be continuous in one dimension for example, dimension 42 and discrete in another dimension, for example dimension 45 or vice versa. One skilled in the art will appreciate that the ultrasound energy may be delivered continuously in both dimensions or discretely in both dimensions.

Figure 8:
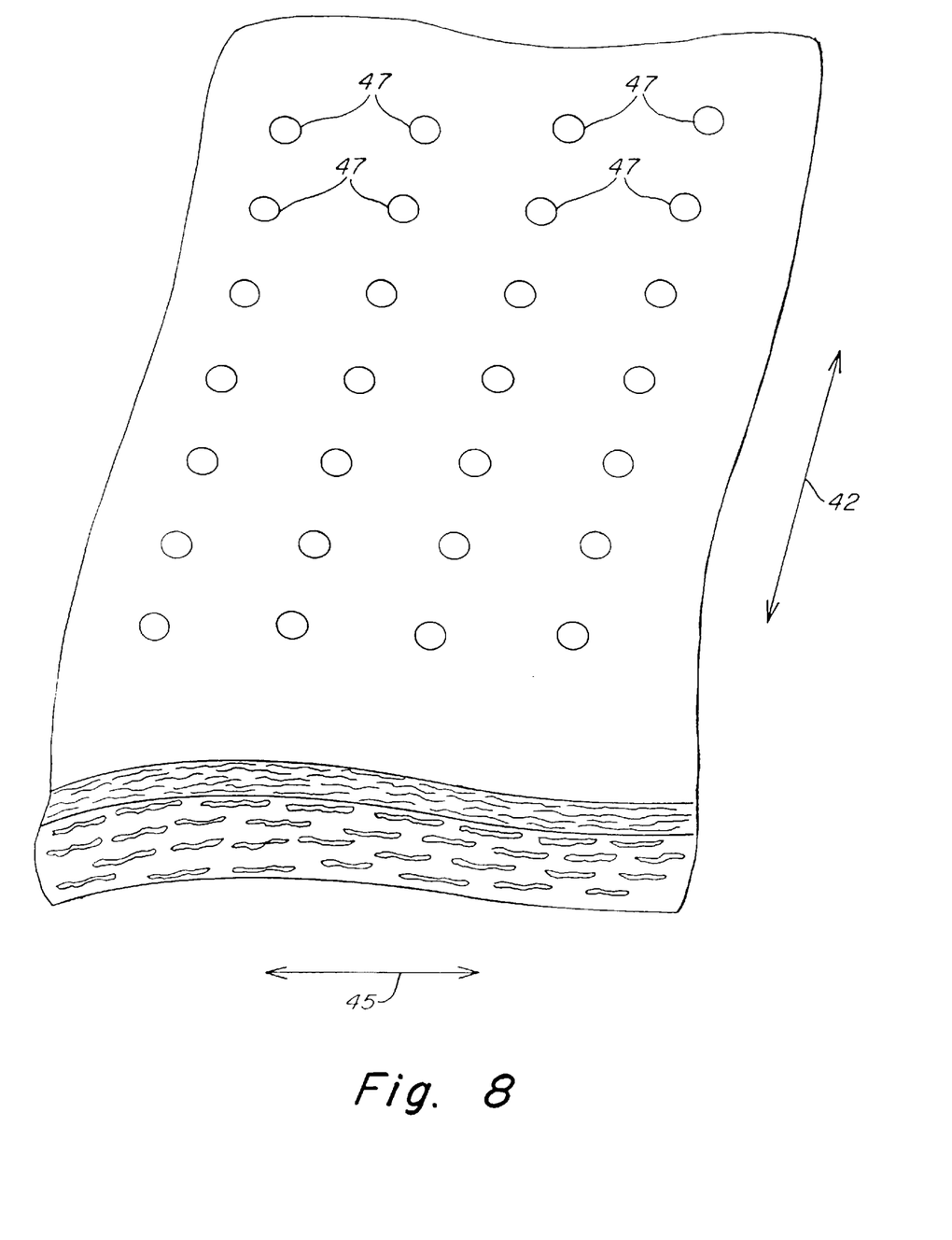
FIG. 8 illustrates a pattern of ultrasound application over a region of skin in accordance with one aspect of the invention.

If the ultrasound energy is delivered discretely in both dimensions 42 and 45, then a pattern of ultrasound energy application such as illustrated in FIG. 8 results where each point 47 represents a location where ultrasound energy has been applied. If the ultrasound energy is applied in a manner that is continuous in both dimensions 42 and 45, then the area in between points 47 would also have ultrasound energy applied thereto.

Figure 9:
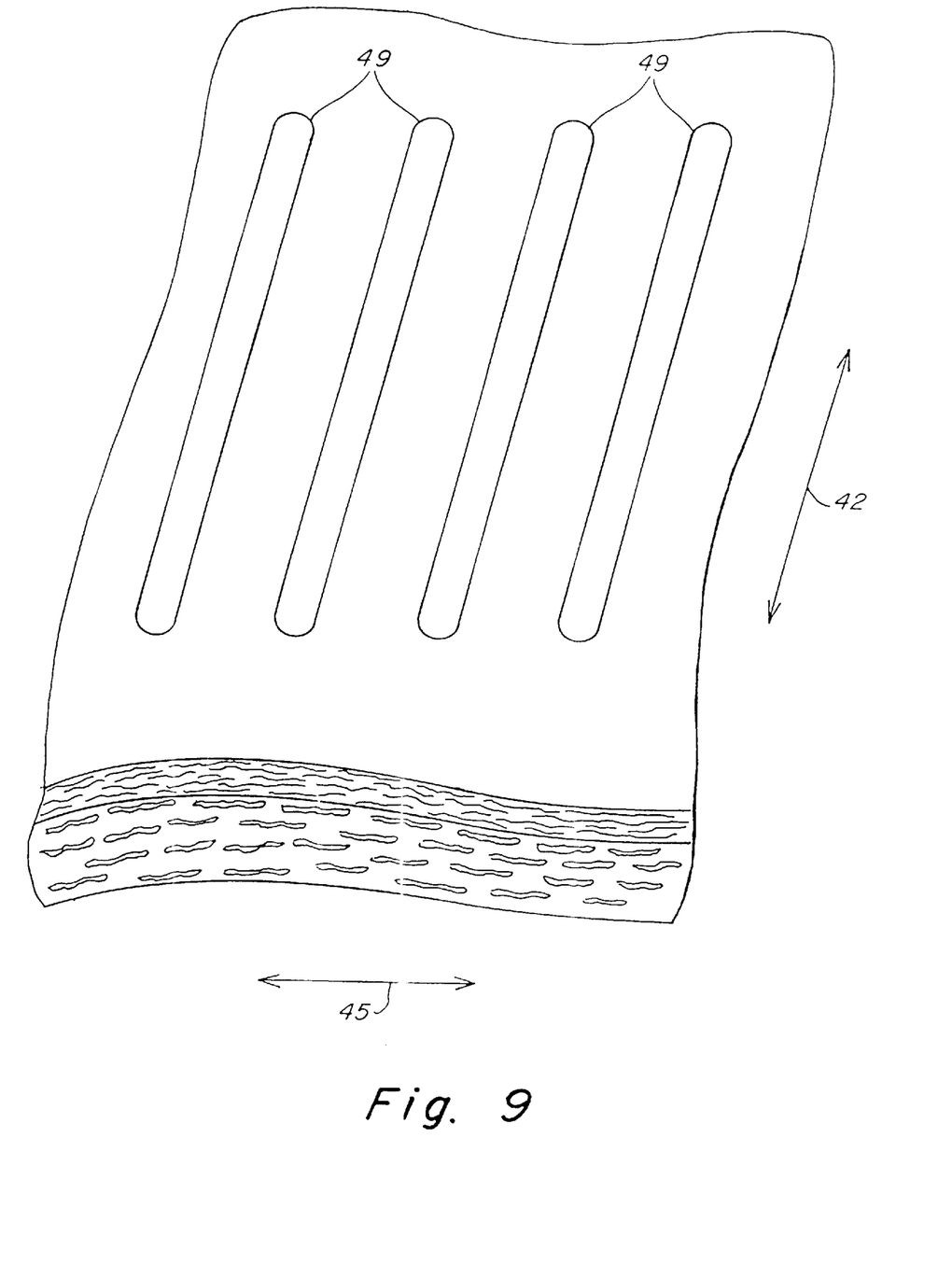
FIG. 9 illustrates a pattern of ultrasound application over a region of skin in accordance with another aspect of the invention.

If the ultrasound energy is delivered discretely in dimension 45 and continuously in dimension 42, then a pattern of ultrasound energy application such as illustrated in FIG. 9 results where regions 49 represent regions where ultrasound energy has been applied.

In the case of continuous ultrasound application, both the speed of scanning along direction 45 and the power being applied must be controlled simultaneously. In the same manner, if discrete application of ultrasound energy is being used, then the distance between points 47 along the direction of arrow 45, the speed with which transducer 22 is moved along the direction of arrow 45, and the timing of individual energy deposition must be controlled to provide homogeneous exposure.

As illustrated in FIGS. 6 and 7 an encoder 124 may be provided. Encoder 124 may be, for example, a wheel that rolls along the skin as the transducer is scanned across the skin. An electrical signal which may be analog or digital in nature, is then provided to controller 102. Controller 102 uses the signal from encoder 124 to determine the speed with which transducer 22 is being scanned across the skin surface and the distance being traveled. With this information, controller 102 can be programmed to adjust the ultrasound pulse frequency and intensity of the ultrasound energy in relation to the scanning speed and distance traveled to achieve, on average, spatially uniform ultrasound dosage if discrete ultrasound pulses are being used. In the same manner, if continuous power is being used, then controller 102 will adjust the ultrasound beam energy in relation to scanning speed to achieve a homogeneous application of ultrasound energy in the target area.

In another embodiment, an acoustically transparent plate may be placed on the skin over the area to be treated and then transducer 22 and encoder 124 are then scanned across the acoustically transparent plate. Scanning the transducer across the plate can also provide a way of delimiting the area to be treated to avoid over-treating or under-treating the area of the skin.

To use the method and apparatus of the invention to reduce or eliminate human skin wrinkles, a physician or technician ("the user") sets a desired depth of the focal point for the ultrasound beam so that the ultrasonic energy is substantially concentrated in the dermis layer of the skin. This depth is typically in the range of five microns to five millimeters. The magnitude of the ultrasound energy to be deposited in the dermis layer in also determined. The duration of treatment and the volume of the dermis layer to be stimulated and/or irritated determine the power level necessary.

The frequency of the ultrasound beam is also chosen. The ultrasound wave frequency should be within the range between approximately 1 megahertz and 500 megahertz. Preferably, the ultrasound beam frequency is relatively low frequency ultrasound between the range of approximately 10 and 80 megahertz. The ultrasound beam frequency chosen is based upon a consideration of the depth of penetration of a given ultrasound frequency wave into the skin and the power required to cause an appropriate stimulation and/or irritation of the dermis region of interest.

Obviously, the above-described steps may be performed in any order.

Once these parameters have been set, the ultrasound transducer is then scanned over the wrinkle area of the skin. Typically, an area much larger than or extending significantly beyond the area occupied by the wrinkle is subjected to the ultrasound beam. Preferably, to be effective, the area of the skin that is subjected to treatment is on the order of ten times larger than the area of the wrinkle itself.

Although the biological mechanism is not completely understood, it appears that hyperthermia and/or cavitation, either alone or in combination, appear to cause a biological response. It appears that denaturation by hyperthermia of at least some of the intracellular proteins, intercellular proteins, and/or enzymes induces a biological or healing response in the body. The biological response results in the synthesis of new connective tissue by fibroblast cells in the dermis in addition to the preexisting connective tissue. The new connective tissue fills out the skin. It is the process of adding new connective tissue to the dermis layer that causes reduction in the appearance of skin wrinkles and improved shape, smoothness, and appearance of the skin.

One mechanism by which the biological response may be stimulated is through hyperthermia. The amount of energy deposited using hyperthermia is typically that required to raise the temperature of the dermis layer to somewhere is the range of 47° C. to 75° C. Preferably, the temperature of the dermis layer that is being treated is increased to between approximately 55° C. and approximately 65° C.

These ranges are selected so as to denature a relatively small fraction of the proteins in the dermis. At a temperature of approximately 47° C., it takes several tens of seconds to denature a small fraction of the proteins in the dermis. By contrast, at a temperature of 73° C., the same small fraction of the proteins in the dermis are denatured in several tens of microseconds. One skilled in the art will appreciate that there is a trade off between exposure time and the amount of energy being applied. The higher the level of energy to be applied, the lower the required exposure time and vice verse. Elevating the dermis layer to a temperature in approximately the range from 55° C. to 65° C. appears to provide a workable compromise between the length of time for the treatment and the amount of energy to be imparted to the skin.

Another mechanism by which a biological response may be induced is cavitation. Preferably, when using cavitation alone or in combination with hyperthermia, enough energy needs to be applied to the dermis to generate, in the dermis, a cavitational bubble. When the bubble collapses, a shock wave results that mechanically, in as localized area, tears apart tissue in the dermis causing dermal inflammation or irritation and a resultant biological response. The biological response results in the synthesis of new connective tissue.

Another mechanism by which a biological response may be induced in through the use of pulsed acoustic waves. Pulsed acoustic waves having sufficient amplitude may be used to create a negative pressure wave at the focal point so as to induce a shock wave type response in the dermis. As with the collapse of the cavitational bubble, the shock wave mechanically, in a localized area, tears apart tissue in the dermis causing a dermal irritation and a resultant biological response. The biological response results in the synthesis of new connective tissue.

It will be appreciated that the magnitude of energy deposited in the skin as a function of the frequency of the ultrasound wave, the time the ultrasound wave is applied, the area of the skin that is treated, thermal diffusion of the heat in the skin, and the impedance of the skin to ultrasound energy may be varied to provide the desired biological response. The present invention typically uses dosages that are significantly lower than conventional hyperthermia therapies. For example, at the surface of the epidermis, the intensity of the ultrasonic waves may be in the range of approximately 100 to 500 watts/cm$^2$. At the focal point in the dermis layer, under some conditions, the intensity of the ultrasonic waves may be in the range of approximately 500 to 1500 watts/cm$^2$.

It should be noted that the method of the present invention does not, following application of ultrasound energy, immediately cause skin wrinkles to be reduced or to disappear. The treatments typically need to be repeated over a long period of time (such as days or months) so that the dermis layer is gently stimulated or irritated to produce the biological response while at the same time avoiding catastrophic damage to the epidermis layer. This has a number of advantages over conventional methods. First, the epidermis is not damaged or is only minimally damaged or effected. Second, the dermis layer is not exposed so the chance of opportunistic infection is reduced. Third, due to the relatively low power levels used and the fact that the epidermis is not catastrophically damaged, the discomfort and pain to the patient compared to conventional methods is considerably reduced.

As noted, the method of the invention using hyperthermia aims to denature a relatively small fraction of the proteins in the dermis, typically less than twenty percent of the proteins. These proteins may be intracellular, extracellular, or also enzymes. Preferably less than ten percent of the proteins in the dermis are denatured and, to be certain that there is much less damage to the cells of the epidermis, no more than approximately five percent of the proteins in the dermis should be denatured.

To further prevent elevation of the temperature or irritation of the epidermis layer of the skin, a cooling device or method may be used. A sapphire tip may be disposed on the ultrasound transducer. Alternatively, water cooling may be used before, during, or after treatment. One skilled in the art will appreciate that there are numerous cooling devices or methods that could be used in conjunction with the invention.

Heating or cooling of the skin can also be used to bring the temperature of the skin to a known state prior to treatment so as to control the dosage of applied ultrasound. This can be significant since denaturation of proteins is dependent on the absolute temperature of the skin and not the relative temperature increase with respect to the starting skin temperature. Heating or cooling of the skin can also be used to take into account patient-to-patient variability such as differing body temperatures to bring all patients to the same state before treatment.

A marker may also be used to delimit treatment areas. The marker may be any kind of suitable marker. For example, a fluorescent gel may be deposited on the skin as the transducer is scanned across the skin. Ink, paint, or disinfectant may also be used. The marker may be visible or may be invisible except when exposed with a suitable light source. A marker allows the user to guide the transducer to produce a spatially uniform ultrasound dosage to ensure uniform stimulation of the dermis and avoid over-treating areas of the skin while under-treating others.

The invention may also reduce other types of defects in skin appearance, such as acne scars and burns, and rejuvenate or refresh skin appearance. This is, as the new connective synthesized in response to the stimulation or irritation of the dermis begins to fill out the dermis, these types of skin defects may become less visible and the skin takes on smoother, refreshed or rejuvenated look.

Having thus described at least one illustrative embodiment of the invention, various alterations, modifications, and improvements will readily occur to those skilled in the art. For example, various alternative acoustic pulse or "shockwave" generators can be employed in lieu of the above described ultrasound transducers. Such alternative energy generators include piezoelectric, electric spark and laser-triggered pulse forming devices operating on rapid state changes of liquid media or on thermoelastic expansion. The pulse generated by these devices can exhibit broad frequency domains. Accordingly, the foregoing description is by way of example only and is not intended as limiting. The invention is limited only as defined in the following claims and the equivalents thereto.

What is claimed is:

1. A method of rejuvenating skin, the method comprising applying an acoustic pulse to a dermis layer below a surface of a region of skin with sufficient intensity and duration, and inducing a shock wave response in the dermis layer and consequent formation of new connective tissue to cause a change in the dermis layer of the skin that results in greater smoothness at the surface of the skin.

2. The method of claim 1, wherein a step of inducing formation of new connective tissue further comprises elevating the temperature of the dermis layer.

3. The method of claim 1, wherein the step of applying an acoustic pulse further includes applying a focused ultrasound beam for a time sufficient to cause proteins in the dermis layer to denature.

4. The method of claim 1, wherein the step of applying an acoustic pulse further comprises applying a power level in the range of approximately 500 W/cm$^2$ to 1500 W/cm$^2$ within a target region of the dermis.

5. The method of claim 1, wherein the step of applying an acoustic pulse to a dermis layer further comprises focusing a ultrasound beam at a depth below the epidermis in a range between approximately 5 microns and 5 millimeters.

6. The method of claim 1, wherein the step of inducing formation of new connective tissue further comprises inducing cavitation in the dermis layer.

7. The method of claim 1, wherein a step of inducing formation of new connective tissue further comprises irritating the dermis layer without adversely damaging the epidermis layer.

8. The method of claim 1, wherein the region of skin includes a wrinkle and the method further comprises the step of scanning the focused ultrasound beam over an area occupied by the wrinkle.

9. The method of claim 8, wherein the step of scanning further comprises scanning the focused ultrasound beam over an area of the skin that is approximately ten times larger than an area of the wrinkle.

10. The method of claim 1, further comprising a step of cooling the region of skin at least one of before, during, or after the step of applying the acoustic pulse.

11. An apparatus for rejuvenating skin, the apparatus comprising:
    an acoustic wave generator for transmitting acoustic waves into a dermis region of skin in response to signals from a driver; and
    a control device constructed and arranged to control the generator to induce shock waves in the dermis layer and the formation of new connective tissue.

12. The apparatus of claim 11, wherein the control device controls the ultrasound waves to elevate the temperature to a range and for a time sufficient to cause proteins in the dermis layer to denature.

13. The apparatus of claim 11, wherein the apparatus further comprises an acoustic lens to focus the acoustic energy at a depth below the epidermis in a range between approximately 5 micrometers and 5 millimeters.

14. The apparatus of claim 11, wherein the control device controls the acoustic waves to have at least one frequency between approximately ten megahertz and one hundred megahertz.

15. The apparatus of claim 11, wherein the apparatus further comprising a temperature sensor coupled to and providing a temperature signal to the control device.

16. The apparatus of claim 11, further comprising an acoustic receiver, coupled to at least one of the acoustic wave generator and the control device.

17. The apparatus of claim 11, further comprising a cooling device that cools the temperature of the epidermis layer.

18. The apparatus of claim 11, wherein the control device controls the acoustic waves to apply a power level in the range of approximately 500 W/cm$^2$ to 1500 W/cm$^2$ within a target region of the dermis.

19. The apparatus of claim 11, wherein the control device controls the acoustic waves to durations ranging from about 10 nanoseconds to about 200 microseconds.

20. An apparatus for rejuvenating skin, the apparatus comprising:
    an acoustic wave generator for delivering acoustic wave energy into a dermis layer of of skin; and
    a controller for driving the acoustic wave generator to deliver pulsed acoustic wave energy at a sufficient amplitude and frequency to induce a shock wave type response in the dermis layer.

21. The apparatus of claim 20, wherein the controller includes circuitry to drive the wave generator to deliver pulsed acoustic wave energy having at least one frequency between approximately ten megahertz and one hundred megahertz to induce a shock wave type response in the dermis layer.

22. An apparatus for rejuvenating skin, the apparatus comprising:
    an acoustic wave generator for delivering acoustic wave energy into a dermis layer of a region of skin; and
    a controller for driving the acoustic wave generator to deliver pulsed acoustic wave energy, the pulses ranging from about 10 nanoseconds to about 200 microseconds in duration, each pulse delivering energy in the range of about 500 W/cm$^2$ to about 1500 W/cm$^2$ at a target site in the dermis layer to induce a shock wave type response in the dermis layer.

23. An apparatus for rejuvenating skin, the apparatus comprising:
    an acoustic wave generator for delivering acoustic wave energy into a dermis layer of skin;
    a controller for driving the acoustic wave generator to deliver pulsed acoustic wave energy at a sufficient amplitude and frequency to induce a shock wave type response in the dermis layer; and
    a linear focusing element for focusing the acoustic energy into a line such that an elongated region of the dermis layer is exposed to the acoustic wave energy.

24. The apparatus of claim 23 wherein the acoustic wave generator comprises at least one ultrasound transducer and the focusing element comprises an elongated surface of the transducer.

25. The apparatus of claim 23 wherein the acoustic wave generator comprises at least on ultrasound transducer and the focusing element comprises at least one cylindrical lens.

26. The apparatus of claim 23, wherein the focusing element focuses the ultrasound energy in a region at a depth below the epidermis in a range between approximately 5 microns and 5 millimeters.

27. An apparatus for rejuvenating skin, the apparatus comprising:
an acoustic wave generator for delivering acoustic wave energy into a dermis layer of skin;
a controller for driving the acoustic wave generator to deliver pulsed acoustic wave energy at a sufficient amplitude and frequency to induce a shock wave type response in the dermis layer; and
a focusing element for focusing the acoustic energy into the dermis layer, the focusing element having a numerical aperture ranging from about 0.1 to about 0.95.

28. The apparatus of claim 27, wherein the controller drives the acoustic wave generator to deliver pulsed acoustic wave energy at sufficient energy to elevate the temperature of a region within the dermis layer, preferably, to a range between approximately 47° C. and 75° C.

29. The apparatus of claim 28, wherein the controller controls the ultrasound waves to elevate a temperature of the dermis layer, preferably, to a range between approximately 55° C. and 65° C.

30. An apparatus for rejuvenating skin, the apparatus comprising:
an acoustic wave generator for delivering acoustic wave energy into a dermis layer of skin;
a linear focusing element for focusing the acoustic energy into a line such that an elongated region of the dermis layer is exposed to the acoustic wave energy to induce a shock wave type response in the dermis layer; and
a scanner for scanning the line through an area within the dermis layer.

31. An apparatus for rejuvenating skin, the apparatus comprising:
an acoustic wave generator for delivering acoustic wave energy into a dermis layer of of skin; and
a controller for driving the acoustic wave generator to deliver pulsed acoustic wave energy at sufficient amplitude to induce a shock wave response in the dermis layer; and
at least one feedback sensor for sensing the effect of the delivered energy and providing a signal to the controller.

32. The apparatus of claim 31, wherein the feedback sensor comprises a temperature sensor coupled to and providing a temperature signal to the controller.

33. The apparatus of claim 31, wherein the feedback sensor comprises an ultrasound receiver, coupled to the ultrasound transducer, and a signal analyzer that processes a signal received by the ultrasound receiver to provide a feedback signal to the controller.

34. The apparatus of claim 31, wherein the feedback sensor comprises an electrical conductivity sensor coupled to and providing to the control device a measure of electrical conductivity in the area of skin where ultrasound energy is being applied.

35. The apparatus of claim 31, wherein the feedback sensor comprises an audio sensor coupled to and providing to the control device an audio signal of the area of skin where ultrasound energy is being applied.

36. The apparatus of claim 35, wherein the audio sensor is a broadband microphone.

37. The apparatus of claim 31, further comprising a cooling device that cools the epidermis layer.

38. An apparatus for rejuvenating skin, the apparatus comprising:
a transducer for delivering acoustic wave energy into a dermis layer of skin; and
an acoustical waveguide disposed at a surface of the transducer, the waveguide having a thickness that defines a depth focus of the ultrasound energy in the skin; wherein the waveguide is further arranged to apply ultrasound shock waves along a longitudinally extended area.

39. The apparatus of claim 38, wherein the waveguide further comprises a cylindrical acoustic lens for applying the ultrasound waves along the longitudinally extended area.

40. The apparatus of claim 38, wherein the waveguide further comprises an acoustically transparent plate for disposition over the area of skin to be treated so as to delimit the area to be treated.

41. The apparatus of claim 38, wherein the waveguide further comprises an acoustic focusing lens has a numerical aperture ranging from about 0.1 to about 0.95.

* * * * *